(12) United States Patent
Kadobayashi (10) Patent No.: US 8,696,355 B2
(45) Date of Patent: Apr. 15, 2014

(54) ARTIFICIAL MOLAR TEETH

(75) Inventor: Yusei Kadobayashi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 445 days.

(21) Appl. No.: 12/714,699

(22) Filed: Mar. 1, 2010

(65) Prior Publication Data
US 2011/0045441 A1   Feb. 24, 2011

(30) Foreign Application Priority Data
Aug. 21, 2009   (JP) ................................. 2009-191963

(51) Int. Cl.
*A61C 13/08* (2006.01)
(52) U.S. Cl.
USPC ........................................................ 433/197
(58) Field of Classification Search
USPC .......... 433/167–172, 181–183, 186, 196–198
See application file for complete search history.

(56) References Cited

U.S. PATENT DOCUMENTS

| 1,665,357 | A | 4/1928 | Gysi |
| 2,104,459 | A | 1/1938 | Gysi |
| 3,105,300 | A | 10/1963 | Beresin |
| 7,267,549 | B2 * | 9/2007 | Monkmeyer .................. 433/197 |

FOREIGN PATENT DOCUMENTS

| GB | 490852 | 8/1938 |
| JP | 2002-177301 | 6/2002 |
| JP | 2006-42954 | 2/2006 |
| WO | 2009/044443 | 4/2009 |

OTHER PUBLICATIONS

Notification of Reason for Refusal (with English translation) issued Apr. 20, 2010 in corresponding to Japanese Patent Application No. 2009-191963.

* cited by examiner

*Primary Examiner* — Sunil K Singh
(74) *Attorney, Agent, or Firm* — Wenderoth, Lind & Ponack, L.L.P.

(57) ABSTRACT

Maxillary molar teeth and mandibular molar teeth are formed so as to be different in intersection angles (vertical line angles) between vertical lines extending in a vertical direction to occlusal facets and occlusal planes. That is, the maxillary molar teeth and the mandibular molar teeth are formed so as to be different in intersection angles of vertical lines of the protrusive occlusal facet and retrusive occlusal facet respectively. The occlusal facets of at least one of buccal cusps of the maxillary molar teeth and lingual cusps of the mandibular molar teeth are designed so that at least one of the width in the mesiodistal direction and the width in the cuspal-cervical direction is smaller than the occlusal facets of the opposite cusps of the antagonist molar teeth.

18 Claims, 6 Drawing Sheets

ARTIFICIAL MOLAR TEETH

BACKGROUND OF THE INVENTION

1. Field of the Invention

The present invention relates to artificial molar teeth which can be arranged easily when making a dental prosthetic appliance and are easy in mastication when dentures are worn and, more particularly to artificial molar teeth in which an angle of occlusal facets of maxillary molar teeth is different from an angle of occlusal facets of mandibular molar teeth.

2. Description of the Related Art

In making a dental prosthetic appliance, it has been considered important to maintain the relation of the cusps and the contour parts of the maxillary and mandibular antagonist molar teeth. Thus, an arrangement of artificial molar teeth has been demanded to be stable in shape by making contact between a plurality of cusps and contour part. It has been further demanded to be free from the work of grinding largely after the arrangement, or changing the surface state largely. However, the arrangement required advanced skill and experience, and it was particularly difficult to arrange the opposing artificial molar teeth in an appropriate positional relation.

JP-A-2002-177301 discloses artificial molar teeth, in which lingual cusps, buccal cusps, and fossae are formed on the occlusal plane of the maxillary molar teeth, and also lingual cusps, buccal cusps, and fossae are formed on the occlusal plane of the antagonist mandibular molar teeth. This artificial molar teeth are configured such that at a central occlusion position, the lingual cusps of the maxillary molar teeth occlude and contact with the fossae of the antagonist mandibular molar teeth, and the buccal cusps of the antagonist mandibular molar teeth occlude and contact with the fossae of the maxillary molar teeth.

The artificial molar teeth of JP-A-2002-177301 occlude and contact at a total of 18 points, that is, 9 points at the left side and 9 points at the right side. In other words, the number of occlusal contact points is smaller than in the full balanced occlusion, and unlike the full balanced occlusion, there is no occlusal contact with the slope surface of the buccal cusp. Accordingly, when making dentures, it is easy to arrange on the wax alveolar ridge, or adjust occlusion by grinding or the like. During use of the dentures, the dentures are stable without falling over. In the masticatory efficiency including grinding, chewing, and cutting of food, an occlusion similar to a full balanced occlusion is obtained. It is further easy to change to the lingualized occlusion not only in making dentures but also in correcting the dentures.

In the artificial molar teeth of JP-A-2002-177301, however, it is required to occlude and contact between the lingual cusps of the maxillary molar teeth and the fossae of the antagonist mandibular molar teeth, and between the fossae of the maxillary molar teeth and the buccal cusps of the antagonist mandibular molar teeth, respectively, and therefore it was extremely difficult to make dentures for each patient depending on the complex oral cavity environment of each patient. Still worse, distortion of molding may occur in the cusps of artificial teeth in a molding process, and therefore it is very difficult to mold the cusps in a shape to be exactly engaged with the fossae of the antagonist molar teeth, causing a disadvantage of poor yield ratio.

JP-A-2006-42954 discloses an occlusion adjusting method in which a cavity of a specified depth is provided in the molar occlusal surface of the mandibular molar teeth configuring the dentures, and the cavity is filled with a resin-made plastic dental material or cast-made inlay wax.

In JP-A-2006-42954, in the occluded state of the maxillary and mandibular teeth of the dentures, by moving the lower jaw to the movable limit in the longitudinal and lateral directions, contacting and passing traces of the lingual cusp tops of the maxillary molar teeth on the occlusal plane of the mandibular molar teeth are recorded on the surface of the plastic dental material or inlay wax as sliding contact marks. By grinding along the sliding contact marks by regular dental technical methods, the state of occlusion can be adjusted.

In the artificial molar teeth of JP-A-2006-42954, however, the cuspal side and the cervical side are molded separately, and it is necessary to adjust occlusion by sampling the motions of the jaws in the oral cavity. Therefore, a process in making denture is long and complicated, and the patient's burden is also large.

SUMMARY OF THE INVENTION

It is an object of the present invention to provide artificial molar teeth capable of being arranged at appropriate positions according to the oral cavity environment of each patient without requiring advanced skill and experience.

To achieve the above object, artificial molar teeth according to a first aspect of the present invention are artificial molar teeth having maxillary molar teeth and mandibular molar teeth arranged in plates to be fitted to the upper jaw and lower jaw in an oral cavity as a dental prosthetic appliance, wherein the maxillary molar teeth and mandibular molar teeth have occlusal facets mutually contacting with each other in each cusp, and an intersection angle of a vertical line extending in a vertical direction to the occlusal facet and an occlusal plane of the maxillary molar teeth is set to be different from an intersection angle of a vertical line extending in a vertical direction to the occlusal facet and an occlusal plane of the mandibular molar teeth.

In these artificial molar teeth, the intersection angle of the vertical line of the occlusal facet and the occlusal plane of the mandibular molar teeth is preferably set to be larger the intersection angle of the vertical line of the occlusal facet and the occlusal plane of the maxillary molar teeth.

The cusp of each molar tooth preferably has a protrusive occlusal facet and a retrusive occlusal facet.

Artificial molar teeth according to a second aspect of the present invention are artificial molar teeth having maxillary molar teeth and mandibular molar teeth arranged in plates to be fitted to the upper jaw and lower jaw in an oral cavity as a dental prosthetic appliance, wherein the maxillary molar teeth and mandibular molar teeth have protrusive occlusal facets and retrusive occlusal facets in each cusp, and the protrusive occlusal facets of the maxillary molar teeth and the mandibular molar teeth mutually contact with each other, and the retrusive occlusal facets of the maxillary molar teeth and the mandibular molar teeth mutually contact with each other, an intersection angle of each vertical line extending in a vertical direction to the protrusive occlusal facet and the retrusive occlusal facet of the maxillary molar teeth is set to be different from the intersection angle of each vertical line extending in a vertical direction to the protrusive occlusal facet and the retrusive occlusal facet of the mandibular molar teeth.

In the second artificial molar teeth, the intersection angle of each vertical line extending in the vertical direction to the protrusive occlusal facet and the retrusive occlusal facet of the maxillary molar teeth is preferably set to be larger than the intersection angle of each vertical line extending in the vertical direction to the protrusive occlusal facet and the retrusive occlusal facet of the mandibular molar teeth.

In these artificial molar teeth, preferably, each protrusive occlusal facet is generally parallel to each other, and each retrusive occlusal facet is generally parallel to each other.

Specifically, each occlusal facet is changed in angle gradually toward the mesial side.

In addition, the occlusal facets are preferably formed in first molar teeth, second molar teeth, and second premolar teeth.

The maxillary molar teeth and the mandibular molar teeth preferably have buccal cusps and lingual cusps, respectively.

The occlusal facet of at least one of the buccal cusp of the maxillary molar teeth and the lingual cusp of the mandibular molar teeth is preferably smaller than the occlusal facet of the opposite cusp of the antagonist molar teeth, at least in one of the width in the mesiodistal direction and the width in the cuspal-cervical direction.

Artificial molar teeth according to a third aspect of the present invention are artificial molar teeth having maxillary molar teeth and mandibular molar teeth arranged in plates to be fitted to the upper jaw and lower jaw in an oral cavity as a dental prosthetic appliance, wherein each molar tooth has an occlusal facet mutually contacting with each other in each cusp, and the occlusal facet of at least one of the buccal cusp of the maxillary molar teeth and the lingual cusp of the mandibular molar teeth is smaller than the occlusal facet of the opposite cusp of the antagonist molar teeth, at least in one of the width in the mesiodistal direction and the width in the cuspal-cervical direction.

According to the artificial teeth of the present invention, the vertical line angle between the vertical line of the occlusal facet of the mandibular molar teeth and the occlusal plane is configured to be different form the vertical line angle between the vertical line of the occlusal facet of the maxillary molar teeth and the occlusal plane. In other words, the intersection angle between the protrusive occlusal facet and the retrusive occlusal facet of the maxillary molar teeth is configured to be different from the intersection angle between the protrusive occlusal facet and the retrusive occlusal facet of the mandibular molar teeth. Accordingly, when arranging the teeth, the mutually opposite sliding occlusal facets of the maxillary molar teeth and the mandibular molar teeth are not positioned in parallel. Accordingly, when arranging the teeth, it is enough to position the molar teeth by adjusting the specified cusps to the fossa of the antagonist molar teeth or the space between molar teeth, and any high precision is not required in the arrangement positions. Hence, when arranging the artificial teeth according to the oral space environment of the patient to make a denture, the maxillary and mandibular molar teeth can be arranged at specified positions without requiring advanced skills and experiences. When molding the artificial molar teeth, high precision is not demanded, and the artificial teeth can be arranged if there is a small deformation. As a result, the manufacturing cost of artificial molar teeth may be substantially reduced.

BRIEF DESCRIPTION OF THE DRAWINGS

Further objects and advantages of the present invention will become clear from the following description taken in conjunction with the preferred embodiments thereof with reference to the accompanying drawings, in which.

DESCRIPTION OF THE PREFERRED EMBODIMENTS

An embodiment of the present invention is described below with reference to the drawings.

The present invention relates to a technique of making artificial teeth as a dental prosthetic appliance as a denture and, especially to a technique capable of applying for making artificial molar teeth. The artificial molar teeth include a first molar tooth, a second molar tooth, a first premolar tooth, and a second premolar tooth, and a combination of at least one pair of maxillary and mandibular antagonist teeth may be preferred.

Figure 1:
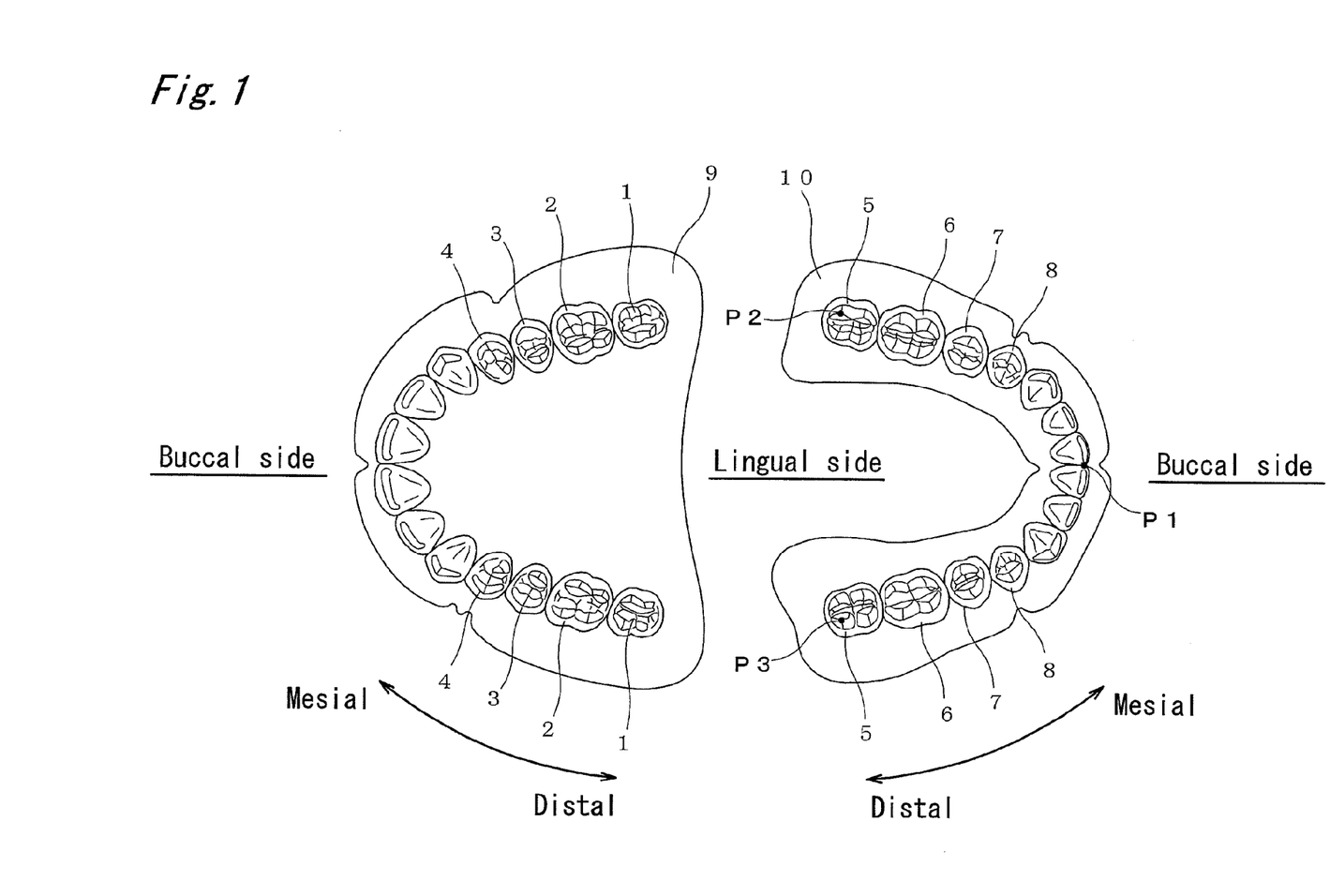
FIG. 1 is a plan view showing a basic configuration of artificial molar teeth to be arranged in the upper jaw and lower jaw.

FIG. 1 shows a general arrangement of all artificial teeth, in which the left side shows the upper jaw, and the right side shows the lower jaw. In the artificial teeth, one maxillary tooth corresponds to one mandibular tooth. The artificial molar teeth may be made of any medical material including ceramic teeth, resin teeth, or composite artificial teeth. In the following explanation, a direction approaching the anterior teeth (central incisor) refers to a mesial side, and an opposite departing direction refers to a distal side. An inward direction to the oral cavity is a lingual side, and an outward direction is a buccal side. A tooth tip direction is a cuspal side, and a tooth root direction is a cervical side.

A basic configuration of the artificial molar teeth is described. As shown in FIG. 1, the artificial molar teeth include a maxillary second molar tooth 1, a maxillary first molar tooth 2, a maxillary second premolar tooth 3, and a maxillary first premolar tooth 4 arranged in the upper jaw, and a mandibular second molar tooth 5, a mandibular first molar tooth 6, a mandibular second premolar tooth 7, and a mandibular first premolar tooth 8 arranged in the lower jaw opposing thereto. The maxillary molar teeth 1 to 4 are arranged in the maxillary plate 9, and the mandibular molar teeth 5 to 8 are arranged in the mandibular plate 10. By way of these plates 9, 10, the teeth are detachably arranged in the oral cavity of the patient. The mandibular plate 10 has a generally U-shape in order to expose the tongue of the patient.

Figure 2:
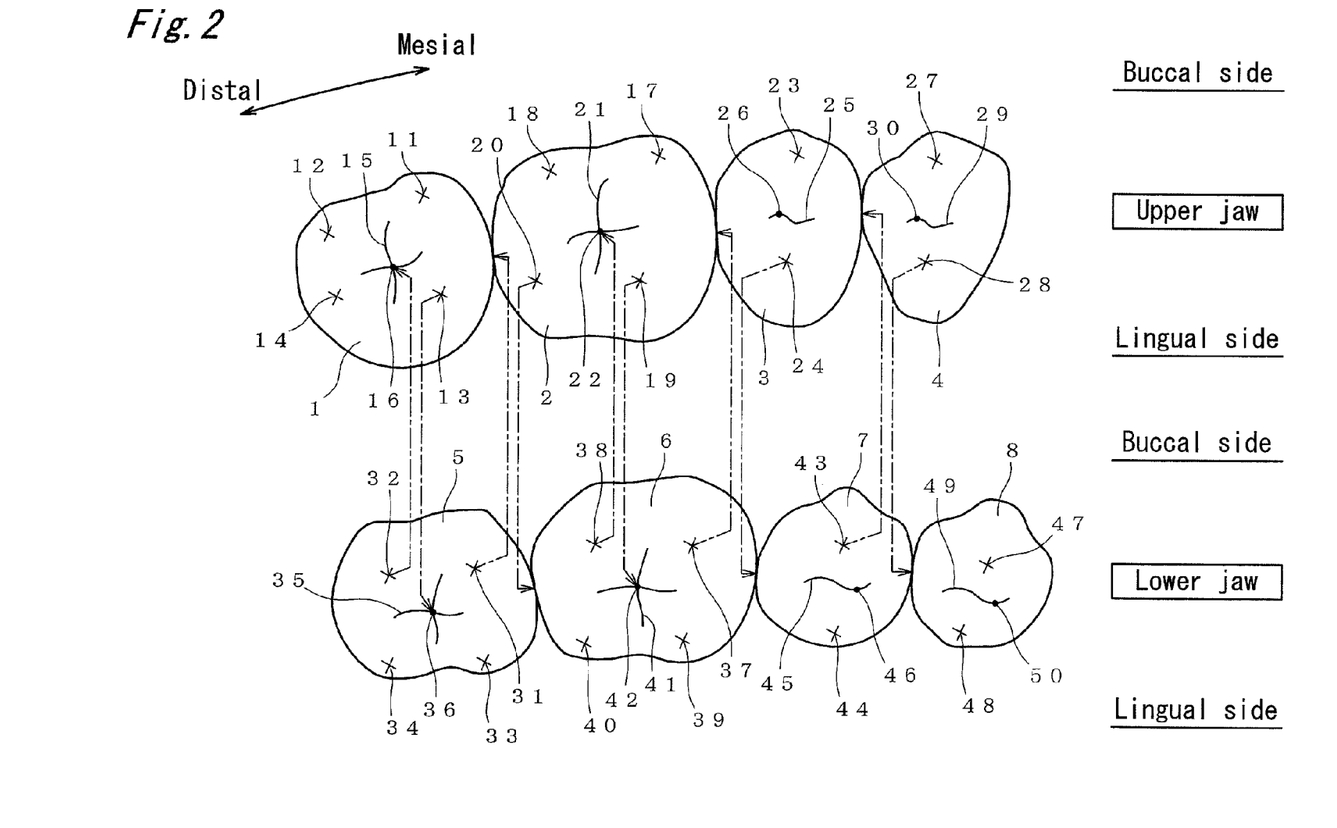
FIG. 2 is a conceptual diagram showing an arranged state of maxillary molar teeth and mandibular molar teeth of the present invention placed in the upper and lower position in the figure respectively.
Figure 3:
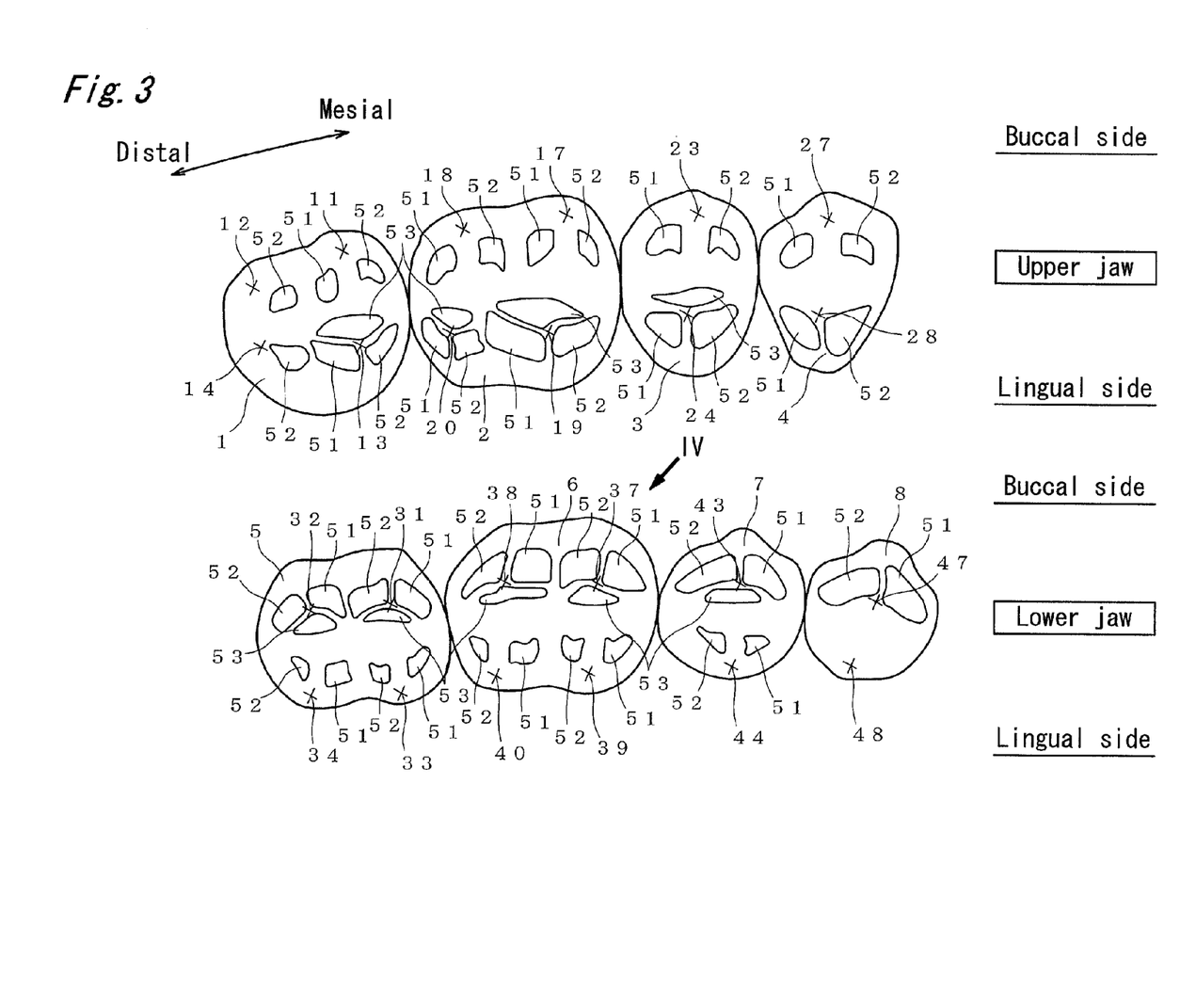
FIG. 3 is a conceptual diagram showing occlusal facets to be formed in the maxillary molar teeth and mandibular molar teeth.

FIGS. 2 and 3 show the relation of the maxillary molar teeth 1 to 4 and the mandibular molar teeth 5 to 8 of the embodiment, arranged in the plates 9, 10, as seen from the maxillary direction. The upper side is the upper jaw as seen from the maxillary direction, and the lower side is the lower jaw as seen from the maxillary direction. However, when the upper jaw is seen from the maxillary direction, the state of occlusion is unknown, and therefore to indicate the state of occlusion, the state of occlusal plane as seen from above is shown. In the figure, the "x"-mark indicates the cusp top of each cusp.

As shown in FIG. 2, the maxillary second molar tooth 1 is provided with a mesial buccal cusp 11 at the mesial side of the buccal side, a distal buccal cusp 12 at the distal side of the buccal side, a mesial lingual cusp 13 at the mesial side of the lingual side, and a distal lingual cusp 14 at the distal side of the lingual side. These cusps 11 to 14 are lumps of tooth substance formed in a shape raised like a taper. The maxillary second molar tooth 1 has a generally cross-shaped groove 15 extending in the mesiodistal direction and the buccal-lingual direction formed by these cusps 11 to 14. At a specified position (intersection position) on this groove 15, a fossa 16 is formed, which has a maximum depth in the vertical direction in the arranged state.

The maxillary first molar tooth 2 is provided with a mesial buccal cusp 17 at the mesial side of the buccal side, a distal buccal cusp 18 at the distal side of the buccal side, a mesial lingual cusp 19 at the mesial side of the lingual side, and a distal lingual cusp 20 at the distal side of the lingual side. These cusps 17 to 20 are lumps of tooth substance formed in a shape raised like a taper. The maxillary first molar tooth 2 has a generally cross-shaped groove 21 extending in the mesiodistal direction and the buccal-lingual direction formed by these cusps 17 to 20. At a specified position on this groove 21, a fossa 22 is formed.

The maxillary second premolar tooth 3 is provided with one buccal cusp 23 at the buccal side, and one lingual cusp 24 at the lingual side. These cusps 23 and 24 are lumps of tooth substance formed in a shape raised like a taper. The maxillary second premolar tooth 3 has a groove 25 extending in the mesiodistal direction formed by these cusps 23, 24. A fossa 26 is formed at a specified position on the groove 25.

The maxillary first premolar tooth 4 is provided with one buccal cusp 27 at the buccal side, and one lingual cusp 28 at the lingual side. These cusps 27 and 28 are lumps of tooth substance formed in a shape raised like a taper. The maxillary first premolar tooth 4 has a groove 29 extending in the mesiodistal direction formed by these cusps 27, 28. A fossa 30 is formed at a specified position on the groove 29.

On the other hand, the mandibular second molar tooth 5 is provided with a mesial buccal cusp 31 at the mesial side of the buccal side, a distal buccal cusp 32 at the distal side of the buccal side, a mesial lingual cusp 33 at the mesial side of the lingual side, and a distal lingual cusp 34 at the distal side of the lingual side. These cusps 31 to 34 are lumps of tooth substance formed in a shape raised like a taper. The mandibular second molar tooth 5 has a generally cross-shaped groove 35 extending in the mesiodistal direction and the buccal-lingual direction formed by these cusps 31 to 34. A fossa 36 is formed at a specified position on the groove 35.

The mandibular first molar tooth 6 is provided with a mesial buccal cusp 37 at the mesial side of the buccal side, a distal buccal cusp 38 at the distal side of the buccal side, a mesial lingual cusp 39 at the mesial side of the lingual side, and a distal lingual cusp 40 at the distal side of the lingual side. The mandibular first molar tooth 6 may be also provided with another cusp at the distal side. These cusps 37 to 40 are lumps of tooth substance formed in a shape raised like a taper. The mandibular first molar tooth 6 has a generally cross-shaped groove 41 extending in the mesiodistal direction and the buccal-lingual direction formed by these cusps 37 to 40. A fossa 42 is formed at a specified position on the groove 41.

The mandibular second premolar tooth 7 is provided with one buccal cusp 43 at the buccal side, and one lingual cusp 44 at the lingual side. These cusps 43 and 44 are lumps of tooth substance formed in a shape raised like a taper. The mandibular second premolar tooth 7 has a groove 45 extending in the mesiodistal direction formed by these 43, 44. A fossa 46 is formed at a specified position on the groove 45.

The mandibular first premolar tooth 8 is provided with one buccal cusp 47 at the buccal side, and one lingual cusp 48 at the lingual side. These cusps 47 and 48 are lumps of tooth substance formed in a shape raised like a taper. The mandibular first premolar tooth 8 has a groove 49 extending in the mesiodistal direction formed by these cusps 47, 48. A fossa 50 is formed at a specified position on the groove 49.

In these molar teeth 1 to 8, sequentially from the distal side, the maxillary second molar tooth 1 and the mandibular second molar tooth 5 are paired and opposite to each other (cusp to fossa), the maxillary first premolar tooth 4 and the mandibular first premolar tooth 8 are paired and opposite to each other, the maxillary second premolar tooth 3 and the mandibular second premolar tooth 7 are paired and opposite to each other, the maxillary first molar tooth 2 and the mandibular first molar tooth 6 are paired and opposite to each other. In the present invention, it is preferred to regard four teeth as a set, that is, maxillary second molar tooth 1, mandibular second molar tooth 5, maxillary first molar tooth 2, and mandibular first molar tooth 6. In addition to these four molar teeth 1, 2, 5, 6, it is also preferred to regard six teeth, by adding the maxillary second premolar tooth 3 and mandibular second premolar tooth 7, as a set. Moreover, in addition to these six molar teeth 1 to 3, 5 to 7, it is also preferred to regard eight teeth, by adding the maxillary first premolar tooth 4 and mandibular first premolar tooth 8, as a set.

Specified cusps of these maxillary molar teeth 1 to 4 and the mandibular molar teeth 5 to 8 are engaged at the central occlusion position with the fossae of the antagonist molar teeth 5 to 8, 1 to 4, or with the spaces between the adjacent antagonist molar teeth 5 to 8, 1 to 4. Specifically, a mesial-lingual cusp 13 of the maxillary second molar tooth 1 is engaged with a fossa 36 of the mandibular second molar tooth 5, a distal-lingual cusp 20 of the maxillary first molar tooth 2 is engaged with a space between the mandibular second molar tooth 5 and the mandibular first molar tooth 6, a mesial-lingual cusp 19 of the maxillary first molar tooth 2 is engaged with a fossa 42 of the mandibular first molar tooth 6, a lingual cusp 24 of the maxillary second premolar tooth 3 is engaged with a space between the mandibular first molar tooth 6 and the mandibular second premolar tooth 7, a lingual cusp 28 of the maxillary first premolar tooth 4 is engaged with a space between the mandibular second premolar tooth 7 and the mandibular first premolar tooth 8. Moreover, a distal-buccal cusp 32 of the mandibular second molar tooth 5 is engaged with the fossa 16 of the maxillary second molar tooth 1, a mesial-buccal cusp 31 of the mandibular second molar tooth 5 is engaged with a space between the maxillary second molar tooth 1 and the maxillary first molar tooth 2, a distal-buccal cusp 38 of the mandibular first molar tooth 6 is engaged with the fossa 22 of the maxillary first molar tooth 2, a mesial-buccal cusp 37 of the mandibular first molar tooth 6 is engaged with a space between the maxillary first molar tooth 2 and the maxillary second premolar tooth 3, and a buccal cusp 43 of the mandibular second premolar tooth 7 is engaged with a space between the maxillary second premolar tooth 3 and the maxillary first premolar tooth 4. The engagement of the cusp with the space means that the entire cusp is engaged with a valley-like space, though the cusp top is abutting against any one of the adjacent molar teeth 1 to 4, 5 to 8.

Figure 4:
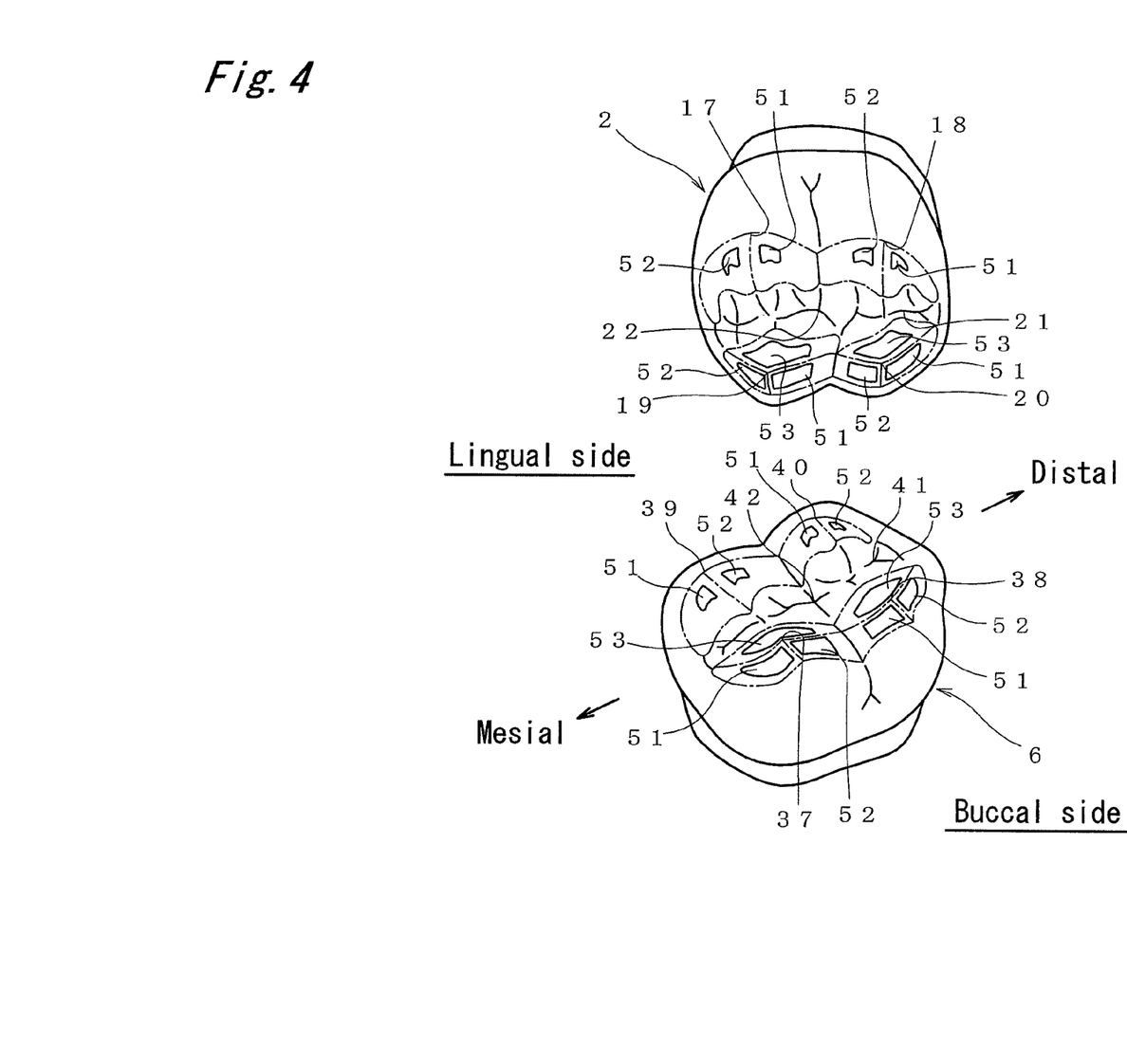
FIG. 4 is a perspective view of the first molar teeth as seen from the direction of IV in FIG. 3.

The molar teeth 1 to 8 of the embodiment are provided with occlusal facets 51 to 53 around each cusp. These occlusal facets 51 to 53 mutually contact (slide) with occlusal facets 51 to 53 of the opposite cusps when the lower jaw is moved in protrusive motion, lateral motion or intermediate motion. These occlusal facets 51 to 53 are shown in FIG. 3. An example of forming position of occlusal facets 51 to 53 opposite in the cusps is shown in FIG. 4, relating to the first molar teeth 2, 6. FIG. 4 is a view as seen from the direction of arrow IV of FIG. 3. In FIG. 4, a single-dot chain line refers to a region forming each one of occlusal facets 51 to 53, and also shows a ridge line formed by the occlusal facets 51 to 53.

The protrusive occlusal facet 51 relates to the balancing function and chewing function in lateral motion or intermediate motion. The protrusive occlusal facet 51 is formed in the maxillary molar teeth 1 to 4, at the distal lingual side of the cusps 11, 13, 17 to 20, 23, 24, 27, 28, and in the mandibular molar teeth 5 to 8, at the mesial buccal side of the cusps 31 to 34, 37 to 40, 43, 44, 47. Meanwhile, the protrusive occlusal facet 51 is not formed at the distal cusps 12, 14 of the maxillary second molar tooth 1, and the lingual cusp 48 of the mandibular first premolar tooth 48, because there is no sliding occlusal plane in relation to the occlusion position.

The retrusive occlusal facet 52 relates to the chewing function in lateral motion or retrusive motion. The retrusive occlusal facet 52 is formed in the maxillary molar teeth 1 to 4, at the mesial lingual side of the cusps 11 to 14, 17 to 20, 23, 24, 27, 28, and in the mandibular molar teeth 5 to 8, at the distal buccal side of the cusps 31 to 34, 37 to 40, 43, 44, 47. Meanwhile, the retrusive occlusal facet 52 is not formed at the lingual cusp 48 of the mandibular first premolar tooth 8, because there is no sliding occlusal plane in relation to the occlusion position.

The balancing occlusal facet 53 relates to the balancing function in lateral motion or retrusive motion. The balancing occlusal facet 53 is formed in the maxillary molar teeth 1 to 3, at the buccal side of the lingual cusps 13, 19, 20, 24, and in the mandibular molar teeth 5 to 7, at the lingual side of the buccal cusps 31, 32, 37, 38, 43. Meanwhile, the balancing occlusal facet 53 is formed so as to make a generally triangular columnar shape, together with the protrusive occlusal facet 51 and retrusive occlusal facet 52. However, the balancing occlusal facet 53 is not formed at the lingual cusp 28 of the maxillary first premolar tooth 4, and at the buccal cusp 47 of the mandibular first premolar tooth 8, because there is no sliding occlusal plane in relation to the occlusion position.

Figure 5:
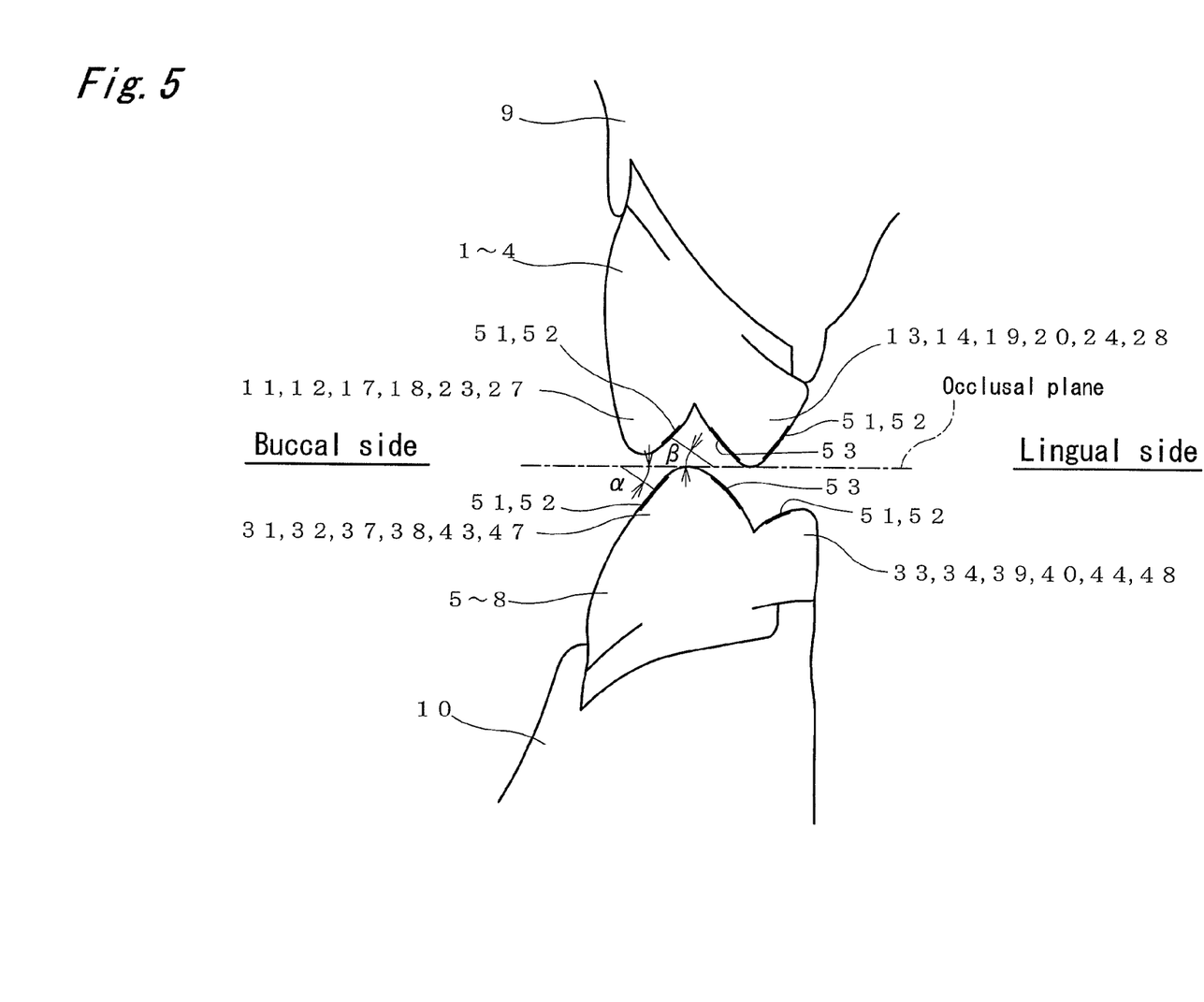
FIG. 5 is a side view of a maxillary molar tooth and a mandibular molar tooth as seen from the mesiodistal direction.

These occlusal facets 51 to 53 are formed as shown in FIG. 5, so that a vertical line may have a specified angle relation to the occlusal plane. The occlusal facets 51 to 53 are not always required to be flat surfaces, but may be spherical surfaces or circular columnar surfaces. In this case, the vertical line is formed of, on any single one of the occlusal facets 51 to 53, a normal line relative to a contact plane containing an intersection or crossing point of a central line between the mesial side outer end position and the distal side outer end position in the mesiodistal direction, and a central line between the cusp side outer end position and the cervical side outer end position in the cusp-cervical direction. The occlusal plane is a plane including middle point P1 of a line between a pair of anterior teeth cutting end corners of the lower jaw in FIG. 1, and distal buccal side cusp tops P2, P3 of a pair of the mandibular second molar teeth 5, 5, and is specific to an articulator on which artificial teeth are installed.

In the embodiment, an intersection angle (hereinafter, referred to as a "vertical line angle") α of each vertical line of the occlusal facets 51 to 53 of the mandibular molar teeth 5 to 8 and the occlusal plane is set to be larger than a vertical line angle β of each vertical line of the occlusal facets 51 to 53 of the maxillary molar teeth 1 to 4 opposite to these occlusal facets 51 to 53 and the occlusal plane (α>β). Specifically, the vertical line angle α of the vertical line of the occlusal facets 51 to 53 of the mandibular molar teeth 5 to 8 and the occlusal plane is set to 5 to 30 degrees in a state that the mandibular molar teeth 5 to 8 are seen in the mesiodistal direction as shown in the figure, preferably 8 to 20 degrees, or more preferably 10 to 15 degrees. By contrast, the vertical line angle β of the vertical line of the occlusal facets 51 to 53 of the maxillary molar teeth 1 to 4 and the occlusal plane is set to be smaller than the vertical line angle α of the mandibular molar teeth 5 to 8, by 0.1 to 2.0 degrees, preferably 0.3 to 0.8 degrees.

In the embodiment, the vertical line angle α of the occlusal facets 51 to 53 of the mandibular molar teeth 5 to 8 and the vertical line angle β of the occlusal facets 51 to 53 of the maxillary molar teeth 1 to 4 are set to be smaller gradually toward the mesial side. For example, in the case of the mandibular molar teeth 5 to 8, in the sequence of distal buccal cusp 32 and mesial buccal cusp 31 of the mandibular second molar tooth 5, distal buccal cusp 38 and mesial buccal cusp 37 of the mandibular first molar tooth 6, buccal cusp 43 of the mandibular second premolar tooth 7, and buccal cusp 47 of the mandibular first premolar tooth 8, the vertical line angle α of the protrusive occlusal facet 51 becomes smaller, and the vertical line angle α of the retrusive occlusal facet 52 becomes smaller. Accordingly, the angle difference of the vertical line angle α of the adjacent occlusal facets 51 to 53 is an acute angle of 0.1 to 3 degrees, preferably 0.3 to 1.7 degrees, or more preferably 0.5 to 0.8 degrees. The total of all angle differences is set within a predetermined allowable range.

This allowable range is a difference between the occlusal facets 51 to 53 of the smallest vertical line angles α, β and the occlusal facets 51 to 53 of the largest vertical line angles α, β and in this embodiment, it is set to be about 10 degrees or less. This allowable range includes an arrangement of forming all inclination angles (vertical line angles α, β) of all occlusal facets 51 to 53 at the same value. That is, the occlusal facets 51 to 53 of the embodiment are formed so that each protrusive occlusal facet 51, each retrusive occlusal facet 52, and each balancing occlusal facet 53 may be generally parallel to each other within the predetermined allowable range.

Moreover, in the embodiment, an intersection angle γ of each vertical line of the protrusive occlusal facet 51 and the retrusive occlusal facet 52 formed on one cusp of the maxillary molar teeth 1 to 4 is formed to be larger than an intersection angle δ of each vertical line of the protrusive occlusal facet 51 and the retrusive occlusal facet 52 formed on the opposite cusp of the antagonist mandibular molar teeth. Herein, the intersection angles γ, δ of vertical lines of the protrusive occlusal facet 51 and the retrusive occlusal facet 52 are defined as angles between vertical lines in a three-dimensional view formed when the vertical line of one of occlusal facets 51, 52 are moved, so as to pass through a point at the intersection of the other occlusal facets 52, 51 with the vertical line thereof. At the central occlusion position of the upper jaw and the lower jaw, each cusp of the maxillary molar teeth 1 to 4 is positioned between the adjacent cusps of the mandibular molar teeth 5 to 8. Herein, the intersection angle γ of the occlusal facets 51, 52 of the maxillary molar teeth 1 to 4 is formed to be larger than each intersection angle δ of the occlusal facets 51, 52 of the pair of cusps positioned at both sides of the mandibular molar teeth 5 to 8. The difference of these intersection angles γ, δ is 0.1 to 2.0 degrees, preferably 0.3 to 0.8 degrees.

Figure 6:
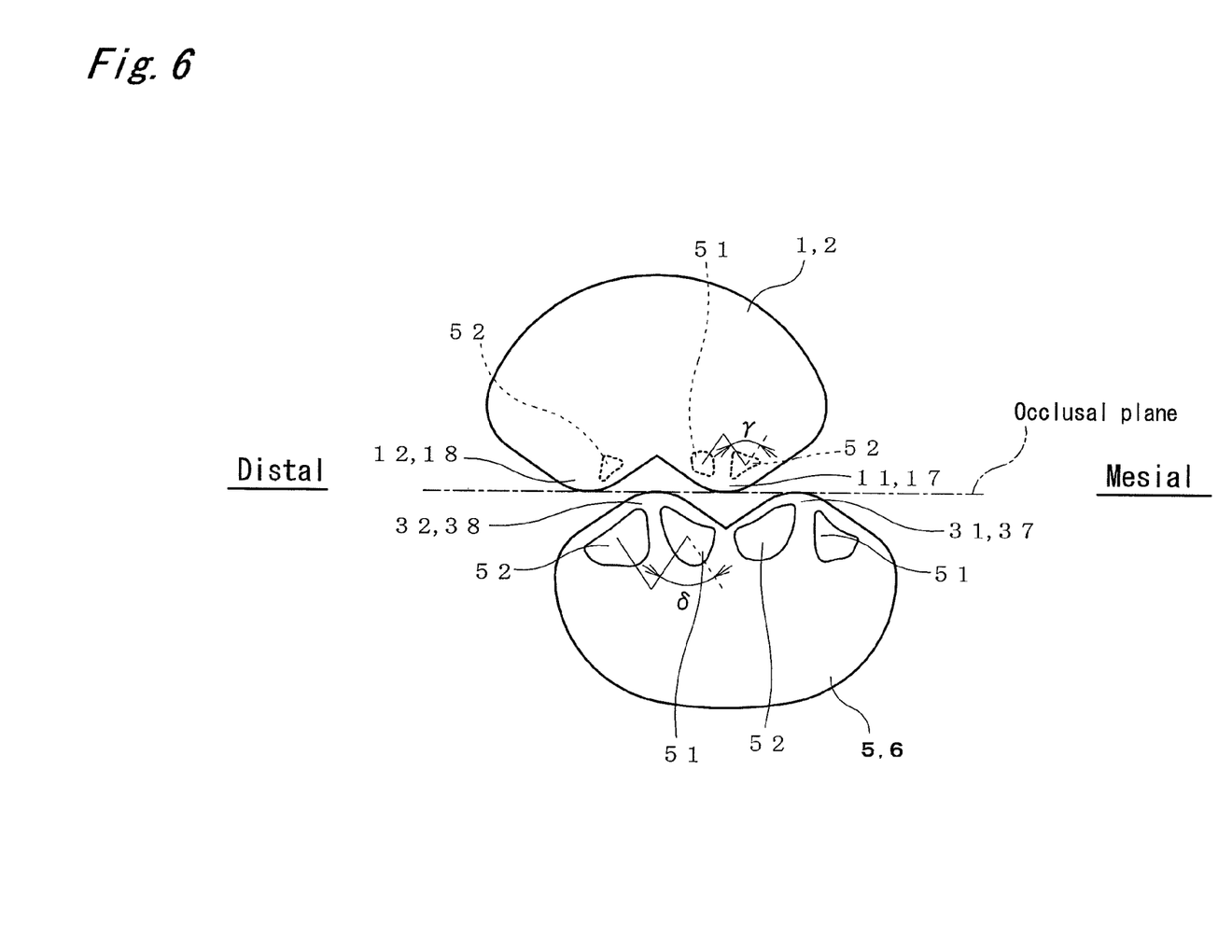
FIG. 6 is a front view of a maxillary molar tooth and a mandibular molar tooth as seen from the buccal side.

In the embodiment, the protrusive occlusal facet 51 and the retrusive occlusal facet 52 formed on the buccal cusps 11, 12, 17, 18, 23, 27 of the maxillary molar teeth 1 to 4 are formed to be smaller in the width in the mesiodistal direction and in the width in the cuspal-cervical direction, as compared with the protrusive occlusal facet 51 and the retrusive occlusal facet 52 formed on the opposite lingual cusps 31, 32, 37, 38, 43, 47 of the mandibular molar teeth 5 to 8 opposing thereto.

Similarly, the protrusive occlusal facet 51 and the retrusive occlusal facet 52 formed on the lingual cusps 33, 34, 39, 40, 44 of the mandibular molar teeth 5 to 8 are formed to be smaller in the width in the mesiodistal direction and in the width in the cuspal-cervical direction, as compared with the protrusive occlusal facet 51 and the retrusive occlusal facet 52 formed on the opposite lingual cusps 13, 14, 19, 20, 24 of the maxillary molar teeth 1 to 4 opposing thereto. Moreover, the occlusal facets 51 to 53 of the mandibular molar teeth 5 to 8 are configured to draw moderate arches at the end portions, as compared with the occlusal facets 51 to 53 of the maxillary molar teeth 1 to 4.

In the artificial molar teeth 1 to 8 formed in this manner, the cusps of the maxillary molar teeth 1 to 4 protrude at a more acute angle (tapered) than the cusps of the mandibular molar teeth 5 to 8. What is more, each cusp of the artificial molar teeth 1 to 8 forms a shape protruding at an acute angle gradually toward the mesial side.

When the artificial molar teeth 1 to 8 are arranged in the plates 9, 10, for example, after arranging the mandibular first premolar tooth 8 in the mandibular plate 10, the maxillary first premolar tooth 4 is arranged in the maxillary plate 9. At this time, these first premolar teeth 4, 8 are occluded with each other, and the buccal cusp 47 of the mandibular first premolar tooth 8 is engaged with the space between the maxillary first premolar tooth 4 and the canine.

Successively, the mandibular second premolar tooth 7 is arranged in the mandibular plate 10, and the maxillary second premolar tooth 3 is arranged in the maxillary plate 9. At this time, these second premolar teeth 3, 7 are arranged so as to contact at one point of the outer circumference with the previously arranged first premolar teeth 4, 8. The second premolar teeth 3, 7 of the upper and lower jaws are occluded with each other, and the lingual cusp 28 of the maxillary first premolar tooth 4 is engaged with the space between the mandibular premolar teeth 7, 8, and the buccal cusp 43 of the mandibular second premolar tooth 7 is engaged with the space between the maxillary premolar teeth 3, 4.

Successively, the mandibular first molar tooth 6 is arranged in the mandibular plate 10, and the maxillary first molar tooth 2 is arranged in the maxillary plate 9. At this time, these first molar teeth 2, 6 are arranged so as to contact at one point of the outer circumference with the previously arranged second premolar teeth 3, 7. The first molar teeth 2, 6 of the upper and lower jaws are occluded with each other, and the mesial lingual cusp 19 of the maxillary first molar tooth 2 is engaged with the fossa 42 of the mandibular first molar tooth 6. By rotating about this point of engagement, the distal buccal cusp 38 of the mandibular first molar tooth 6 is adjusted to be engaged with the fossa 22 of the maxillary first molar tooth 2.

Finally, the mandibular second molar tooth 5 is arranged in the mandibular plate 10, and the maxillary second molar tooth 1 is arranged in the maxillary plate 9. At this time, these second molar teeth 1, 5 are arranged so as to contact at one point of the outer circumference with the previously arranged first molar teeth 2, 6. The second molar teeth 1, 5 of the upper and lower jaws are occluded with each other, and the mesial lingual cusp 13 of the maxillary second molar tooth 1 is engaged with the fossa 36 of the mandibular second molar tooth 5. By rotating about this point of engagement, the distal buccal cusp 32 of the mandibular second molar tooth 5 is adjusted to be engaged with the fossa 16 of the maxillary second molar tooth 1.

Herein, in the molar teeth 1 to 8 having the occlusal facets 51 to 53 on each cusp in the embodiment, the occlusal facets 51 to 53 of the maxillary molar teeth 1 to 4 slide oppositely on the occlusal facets 51 to 53 of the mandibular molar teeth 5 to 8 opposing thereto. In the embodiment, however, the vertical line angle $\alpha$ of the vertical line and the occlusal plane of the occlusal facets 51 to 53 of the mandibular molar teeth 5 to 8 is formed to be different from the vertical line angle $\beta$ of the vertical line and the occlusal plane of the occlusal facets 51 to 53 of the maxillary molar teeth 1 to 4. In other words, the intersection angle $\gamma$ of the protrusive occlusal facet 51 and the retrusive occlusal facet 52 of the maxillary molar teeth 1 to 4 is different from the intersection angle $\delta$ of the protrusive occlusal facet 51 and the retrusive occlusal facet 52 of the mandibular molar teeth 5 to 8. Accordingly, when arranging the teeth, the mutually opposite sliding occlusal facets 51 to 53 of the maxillary molar teeth 1 to 4 and the mandibular molar teeth 5 to 8 are not positioned in parallel. That is, when arranging the teeth, since it is enough to arrange the molar teeth 1 to 4, 5 to 8 by positioning the specified cusps in the fossa or space of the molar teeth 1 to 4, 5 to 8, high precision is not needed in the arrangement positions.

Hence, when making a denture according to the oral cavity of the patient in arrangement of teeth, the maxillary and mandibular molar teeth 1 to 4, 5 to 8 can be arranged in specified positions without having advanced skill and experience. When molding the artificial molar teeth 1 to 8, high precision is not needed, and the artificial teeth can be arranged even if there is a slight deformation. As a result, the manufacturing cost of artificial molar teeth 1 to 8 can be substantially curtailed.

Moreover, the oral cavities of patients are very large in individual difference, and in clinical cases of edentulous jaw, the space, thealveolar ridge height, and angle in the oval cavity are largely different. In such varied clinical cases, the artificial molar teeth can be arranged easily and in a short time, and the situation in the oral cavity can be reproduced. In the presence of a residual tooth, it was previously difficult to arrange the artificial molar teeth 1 to 8 at specified positions, but the occlusion position of the upper and lower jaws can be adjusted easily. As a result, the aesthetic appearance of the oral cavity after installation of the prosthesis is enhanced.

In the embodiment, when arranging the maxillary molar teeth 1 to 4 and the mandibular molar teeth 5 to 8, from the mesial side, maxillary and mandibular pairs of first premolar teeth 4, 8, second premolar teeth 3, 7, first molar teeth 2, 6, and second molar teeth 1, 5 are arranged sequentially, but the same operation and effect will be obtained even if the mandibular molar teeth 8 to 5 are arranged from the mesial side, and the maxillary molar teeth 1 to 4 are arranged from the mesial side, and they are adjusted later.

These arranged molar teeth 1 to 8 are naturally worn and become parallel in the course of years of use after the occlusal facets 51 to 53 are arranged at different inclination angles in each cusp. More specifically, when the lower jaw is moved in protrusive motion, lateral motion, or intermediate motion, the mutually opposite protrusive occlusal facets 51, 51, the mutually opposite retrusive occlusal facets 52, 52, and the mutually opposite balancing occlusal facets 53, 53 are worn out by sliding against each other. Consequently, as the mutually sliding occlusal facets 51 to 53 become parallel to each other, in addition to the cutting function, the grinding function is improved, and it becomes easier to chew.

In the embodiment, the protrusive occlusal facet 51 and the retrusive occlusal facet 52 formed on the buccal cusps 11, 12, 17, 18, 23, 27 of the maxillary molar teeth 1 to 4 positioned most closely to the buccal side are formed smaller than the opposite (sliding) occlusal facets 51, 52. Therefore, when the lower jaw is moved in lateral motion, for example, the buccal cusps 11, 12, 17, 18, 23, 27 of the maxillary molar teeth 1 to 4 do not contact closely with the cusp top, and biting of cheek or tongue may be prevented. Similarly, the protrusive occlusal facet 51 and the retrusive occlusal facet 52 formed on the buccal cusps 33, 34, 39, 40, 44 of the mandibular molar teeth 5 to 8 positioned most closely to the lingual side are formed smaller in the width of mesiodistal direction and in the width of cuspal-cervical direction, than the opposite occlusal facets 51, 52. Therefore, when the lower jaw is moved in lateral motion, for example, the buccal cusps 33, 34, 39, 40, 44 of the mandibular molar teeth 5 to 8 do not contact closely with cusp tops, and therefore biting of the tongue may be prevented.

Mastication is usually carried out while crushing the food, and food chips are likely to exist between teeth, and there is no escape space for food if both of the occlusal facets 51, 52 are large. Similarly, when grinding the food, if the occlusal facets 51, 52 of the upper and lower jaws are large, there is no space protrusive for the food, and sufficient chewing is difficult. In the embodiment, however, since the occlusal facets 51, 52 of the buccal cusps of the maxillary molar teeth 1 to 4 and the lingual cusps of the mandibular molar teeth 5 to 8 are small, such problems are avoided, and the chewing effect is enhanced if the pressure of occlusion is small.

The artificial teeth of the present invention is not limited to the above embodiment, but may be modified in various manners.

For example, in the embodiment, the vertical line angle α of the occlusal facets 51 to 53 and the occlusal plane of the mandibular molar teeth 5 to 8 is set larger than the vertical line angle β of the occlusal facets 51 to 53 and the occlusal plane of the maxillary molar teeth 1 to 4, but the vertical line angle α of the occlusal facets 51 to 53 and the occlusal plane of the mandibular molar teeth 5 to 8 may be set smaller than the vertical line angle β of the occlusal facets 51 to 53 and the occlusal plane of the maxillary molar teeth 1 to 4. In this case, the intersection angle γ of each vertical line of the protrusive occlusal facet 51 and the retrusive occlusal facet 52 of the maxillary molar teeth 1 to 4 is smaller than the intersection angle δ of each vertical line of the protrusive occlusal facet 51 and the retrusive occlusal facet 52 of the mandibular molar teeth 5 to 8.

In the embodiment, both the protrusive occlusal facet 51 and the retrusive occlusal facet 52 formed in the buccal cusps 11, 12, 17, 18, 23, 27 of the maxillary molar teeth 1 to 4 and formed in the lingual cusps 33, 34, 39, 40, 44 of the mandibular molar teeth 5 to 8 are set smaller in the width in the mesiodistal direction and the cuspal-cervical direction, but either one of the protrusive occlusal facet 51 and the retrusive occlusal facet 52 may be set smaller. Or the width may be set smaller in either one of the mesiodistal direction and the cuspal-cervical direction.

Although the present invention has been fully described by way of the examples with reference to the accompanying drawings, it is to be noted here that various changes and modifications will be apparent to those skilled in the art. Therefore, unless such changes and modifications otherwise depart from the spirit and scope of the present invention, they should be construed as being included therein.

What is claimed is:

1. Artificial molar teeth having maxillary molar teeth and mandibular molar teeth arranged in plates to be fitted to the upper jaw and lower jaw, respectively, in an oral cavity as a dental prosthetic appliance,
    wherein the maxillary molar teeth and the mandibular molar teeth have occlusal facets mutually contacting with each other in each cusp,
    wherein each of the maxillary molar teeth has an occlusal facet that defines an intersection angle β formed by a first line that is normal to the occlusal facet of the maxillary molar tooth and an occlusal plane,
    wherein each of the mandibular molar teeth has an occlusal facet that defines an intersection angle α formed by a second line that is normal to the occlusal facet of the mandibular molar tooth and the occlusal plane,
    wherein, for each of the maxillary molar teeth, the first line that is normal to the occlusal facet is a normal line relative to a contact plane containing a crossing point of a central line between a mesial side outer end position and a distal side outer end position in the mesiodistal direction, and a central line between a cusp side outer end position and a cervical side outer end position in the cusp-cervical direction of the maxillary molar tooth,
    wherein, for each of the mandibular molar teeth, the second line that is normal to the occlusal facet is a normal line relative to a contact plane containing a crossing point of a central line between a mesial side outer end position and a distal side outer end position in the mesiodistal direction, and a central line between a cusp side outer end position and a cervical side outer end position in the cusp-cervical direction of the mandibular molar tooth,
    wherein the occlusal plane is a plane including a middle point of a line between a pair of anterior teeth cutting end corners of the lower jaw, and distal buccal side cusp tops of a pair of mandibular second molar teeth,
    wherein the intersection angle α of the mandibular molar teeth is larger than the intersection angle β of the maxillary molar teeth,
    wherein, among the maxillary molar teeth, the intersection angle β becomes smaller toward the mesial side, and
    wherein, among the mandibular molar teeth, the intersection angle α becomes smaller toward the mesial side.

2. The artificial molar teeth of claim 1, wherein the cusp of each molar tooth has a protrusive occlusal facet and a retrusive occlusal facet.

3. The artificial molar teeth of claims 2, wherein the protrusive occlusal facets are generally parallel to each other, and the retrusive occlusal facets are generally parallel to each other.

4. The artificial molar teeth of claim 3, wherein the angle of the occlusal facets vary among the molar teeth in the mesiodistal direction.

5. The artificial molar teeth of claim 1, wherein the occlusal facets are formed in first molar teeth, second molar teeth, and second premolar teeth.

6. The artificial molar teeth of claim 1, wherein the maxillary molar teeth and the mandibular molar teeth have buccal cusps and lingual cusps, respectively.

7. The artificial molar teeth of claim 6, wherein the occlusal facet of at least one of the buccal cusp of the maxillary molar teeth and the lingual cusp of the mandibular molar teeth is smaller than the occlusal facet of the opposite cusp of the antagonist molar teeth, at least in one of the width in the mesiodistal direction and the width in the cuspal-cervical direction.

8. The artificial molar teeth of claim 1, wherein the intersection angle β of the maxillary molar teeth is smaller than the intersection angle α of the mandibular molar teeth by 0.1 to 2 degrees.

9. The artificial molar teeth of claim 1, wherein the intersection angle β of the maxillary molar teeth is smaller than the intersection angle α of the mandibular molar teeth by 0.3 to 0.8 degrees.

10. The artificial molar teeth of claim 1, wherein the cusp of each of the molar teeth has a protrusive occlusal facet and a retrusive occlusal facet, wherein, among the maxillary molar teeth, the intersection angle β becomes smaller for each occlusal facet in a direction toward the mesial side, and wherein, among the mandibular molar teeth, the intersection angle α becomes smaller for each occlusal facet in a direction toward the mesial side.

11. The artificial molar teeth of claim 10, wherein the intersection angle β of the maxillary molar teeth is smaller than the intersection angle α of the mandibular molar teeth by 0.1 to 2 degrees.

12. The artificial molar teeth of claim 10, wherein the intersection angle β of the maxillary molar teeth is smaller than the intersection angle α of the mandibular molar teeth by 0.3 to 0.8 degrees.

13. Artificial molar teeth having a maxillary molar tooth and a mandibular molar tooth arranged in plates to be fitted to the upper jaw and lower jaw, respectively, in an oral cavity as a dental prosthetic appliance, wherein the maxillary molar tooth and the mandibular molar tooth have protrusive occlusal facets and retrusive occlusal facets in each cusp, and the protrusive occlusal facets of the maxillary molar tooth and the mandibular molar tooth mutually contact with each other, and the retrusive occlusal facets of the maxillary molar tooth and the mandibular molar tooth mutually contact with each other, an intersection angle γ formed by a first line that is normal to the protrusive occlusal facet and a second line that is normal to the retrusive occlusal facet of the maxillary molar teeth is set to be different from an intersection angle δ formed by a third line that is normal to the protrusive occlusal facet and a fourth line that is normal to the retrusive occlusal facet of the mandibular molar teeth, wherein the first line that is normal to the protrusive occlusal facet is a normal line relative to a contact plane containing a crossing point of a central line between a mesial side outer end position and a distal side outer end position in the mesiodistal direction, and a central line between a cusp side outer end position and a cervical side outer end position in the cusp-cervical direction of the maxillary molar tooth, wherein the second line that is normal to the retrusive occlusal facet is a normal line relative to a contact plane containing a crossing point of a central line between a mesial side outer end position and a distal side outer end position in the mesiodistal direction, and a central line between a cusp side outer end position and a cervical side outer end position in the cusp-cervical direction of the maxillary molar tooth, wherein the third line that is normal to the protrusive occlusal facet is a normal line relative to a contact plane containing a crossing point of a central line between a mesial side outer end position and a distal side outer end position in the mesiodistal direction, and a central line between a cusp side outer end position and a cervical side outer end position in the cusp-cervical direction of the mandibular molar tooth, wherein the fourth line that is normal to the retrusive occlusal facet is a normal line relative to a contact plane containing a crossing point of a central line between a mesial side outer end position and a distal side outer end position in the mesiodistal direction, and a central line between a cusp side outer end position and a cervical side outer end position in the cusp-cervical direction of the mandibular molar tooth, and wherein the intersection angle γ of the maxillary molar tooth is set to be larger than the intersection angle δ of the mandibular molar tooth.

14. The artificial molar teeth of claim 13, wherein the protrusive occlusal facets are generally parallel to each other, and the retrusive occlusal facets are generally parallel to each other.

15. The artificial molar teeth of claim 14, wherein each occlusal facet is changed in angle gradually toward the mesial side.

16. The artificial molar teeth of claim 13, wherein the occlusal facets are formed in first molar teeth, second molar teeth, and second premolar teeth.

17. The artificial molar teeth of claim 13, wherein the maxillary molar teeth and the mandibular molar teeth have buccal cusps and lingual cusps, respectively.

18. The artificial molar teeth of claim 17, wherein the occlusal facet of at least one of the buccal cusp of the maxillary molar teeth and the lingual cusp of the mandibular molar teeth is smaller than the occlusal facet of the opposite cusp of the antagonist molar teeth, at least in one of the width in the mesiodistal direction and the width in the cuspal-cervical direction.

* * * * *